United States Patent [19]
Kokubo

[11] Patent Number: 5,737,280
[45] Date of Patent: Apr. 7, 1998

[54] CLOCKING SYSTEM FOR MEASURING RUNNING SPEEDS OF TRACK RUNNERS

[75] Inventor: Hiroshi Kokubo, Kyoto, Japan

[73] Assignee: Univert Inc., Osaka, Japan

[21] Appl. No.: 561,580

[22] Filed: Nov. 21, 1995

[30] Foreign Application Priority Data

Nov. 21, 1994 [JP] Japan .................. 6-309483

[51] Int. Cl.$^6$ .............. G04F 8/00; G04B 47/00; G06K 7/10; G01C 22/00
[52] U.S. Cl. .................. 368/2; 368/3; 368/10; 235/377; 340/323 R; 377/20; 377/24.2
[58] Field of Search ................. 368/2, 3, 9–11, 368/110–113; 364/569; 377/20, 24, 24.2; 235/377, 380–385

[56] References Cited

U.S. PATENT DOCUMENTS

| | | | |
|---|---|---|---|
| 4,571,698 | 2/1986 | Armstrong | 364/569 |
| 4,823,367 | 4/1989 | Kreutzfeld | 377/24.2 |
| 5,196,846 | 3/1993 | Brockelsry | 340/933 |
| 5,245,162 | 9/1993 | Takahashi | 235/377 |
| 5,245,346 | 9/1993 | Nishimura et al. | 342/42 |
| 5,436,611 | 7/1995 | Arlinghaus, Jr. | 340/323 R |
| 5,511,045 | 4/1996 | Sasaki et al. | 368/2 |
| 5,538,007 | 7/1996 | Gorman | 728/710 |

*Primary Examiner*—Vit W. Miska
*Attorney, Agent, or Firm*—Oblon, Spivak, McClelland, Maier & Neustadt, P.C.

[57] ABSTRACT

A clocking system for measuring running speeds such as split time or lap time for a plural number of track runners like racehorses at each one of a plural number of clocking positions provided at predetermined intervals along a running course or track toward a goal position. The clocking system fundamentally includes: a trigger signal transmission means provided at each one of the clocking positions and adapted to release a trigger signal toward a narrow signal receiving zone; a passing signal generating means carried by each runner and adapted to produce a passing signal specific to a particular runner at each clocking position upon reception of the trigger signal; and a measuring means provided either at each clocking position or on each runner and adapted to register a time reading for each runner upon reception of the trigger signal or passing signal. The measuring means can be arranged to include a sensor or a number of sensor means for collecting physical data of the runner during a run on an exercising track in addition to and in relation with the clocking operation.

12 Claims, 14 Drawing Sheets

FIG. 5A
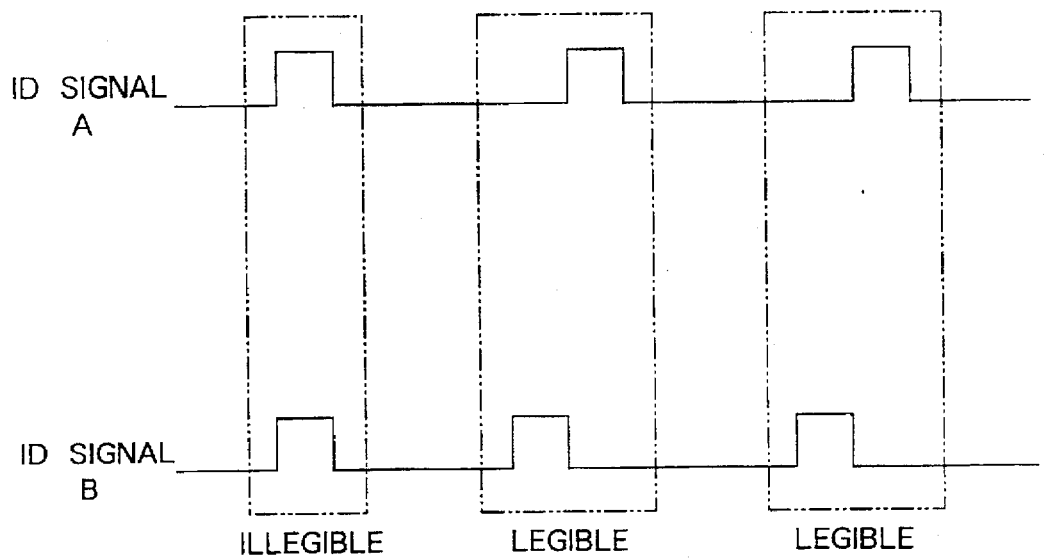
FIG. 5B
FIG. 7
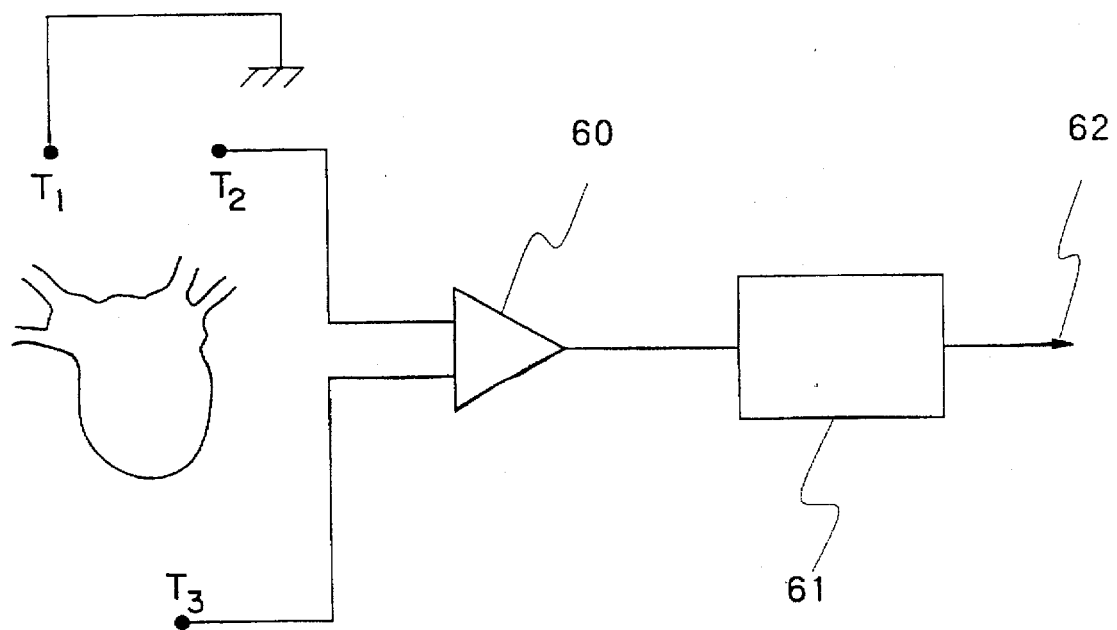

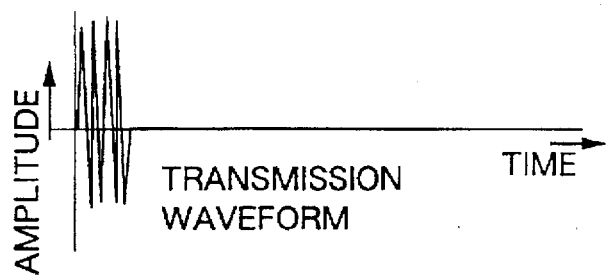
FIG. 13A
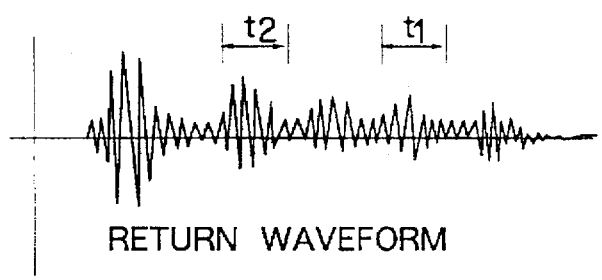
FIG. 13B
FIG. 14
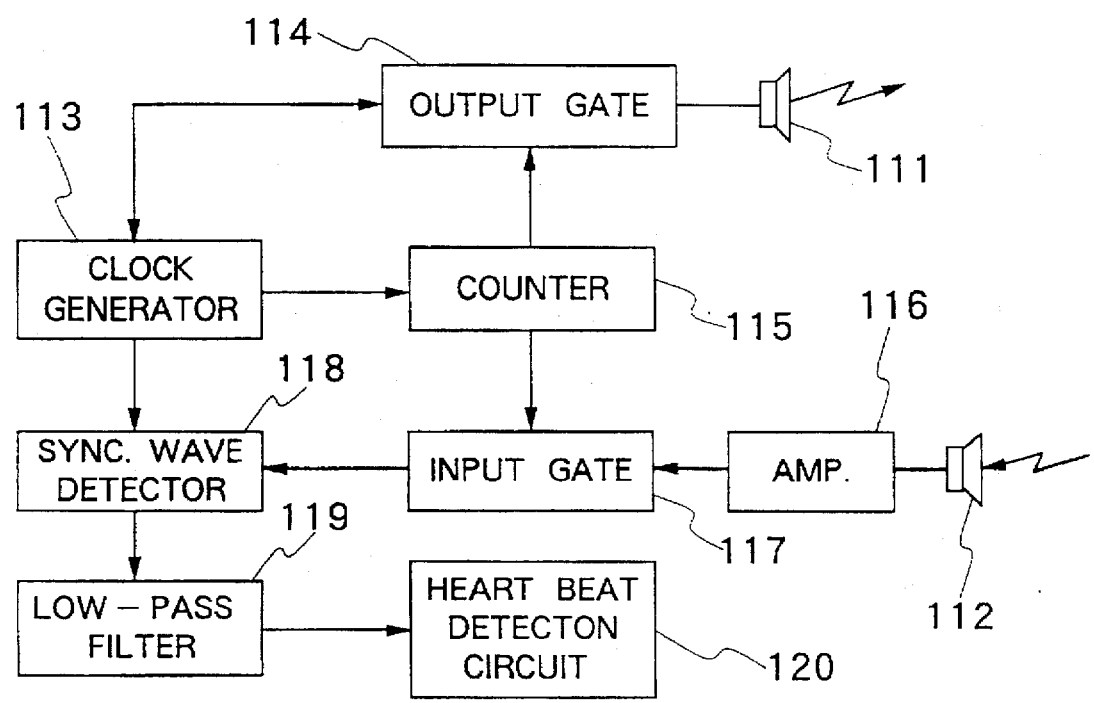

FIG. 17A
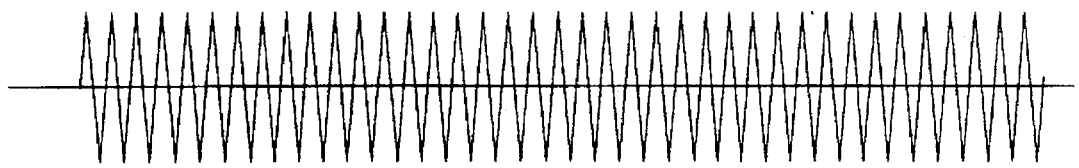
FIG. 17B
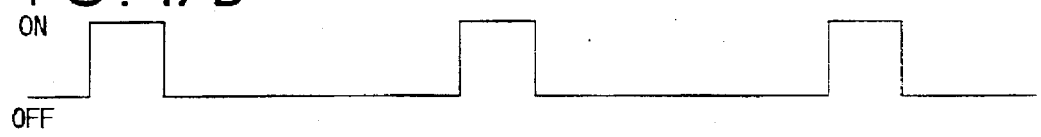
FIG. 17C
FIG. 17D
FIG. 17E
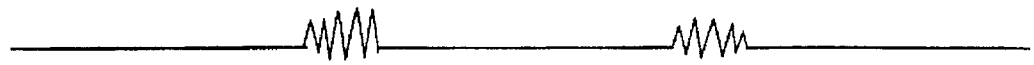

F I G. 18A
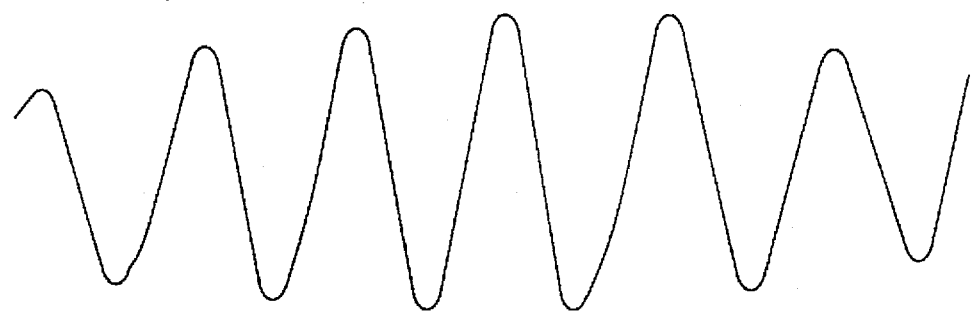
F I G. 18B
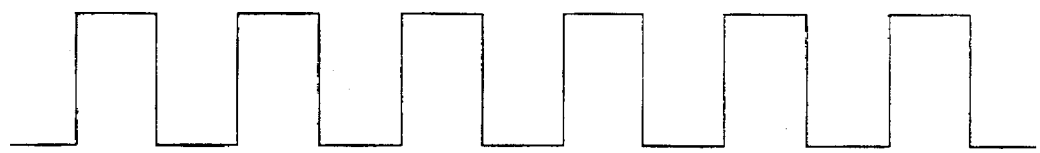
F I G. 18C
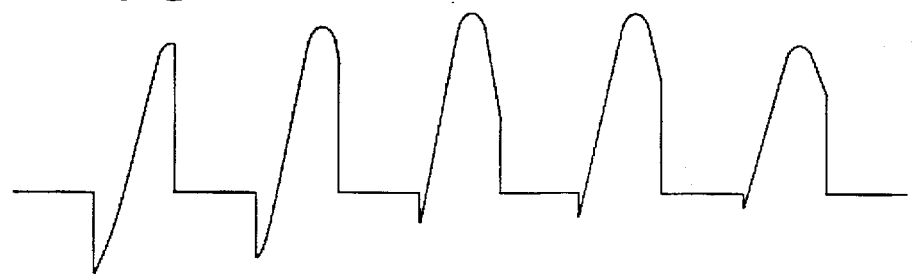
F I G. 18D
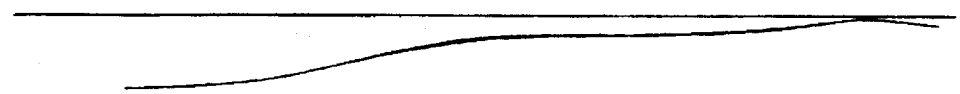

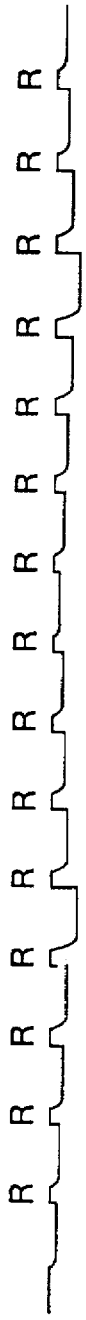
FIG. 19A
FIG. 19B
FIG. 19C
FIG. 19D
FIG. 19E

5,737,280

CLOCKING SYSTEM FOR MEASURING RUNNING SPEEDS OF TRACK RUNNERS

BACKGROUND OF THE INVENTION

1. Field of the Art

This invention relates to a clocking system for measuring running speeds of track runners, and more particularly to a clocking system which incorporates electrical or ultrasonic sensor means for monitoring physical conditions of individual runners working on an exercising track or the like, in relation with a clocking operation measuring lap times or split times at predetermined clocking points for individual runner on the track.

2. Prior Art

For instance, in mounted exercises of racehorses on a training track, it has been the usual practice to judge the progress of a training process or fitness or ability of individual racehorses on the basis of clock readings of runs over a predetermined distance of the training track. When working racehorses on a training track, normally the running pace is gradually increased from a start point instead of dashing off at a high speed, letting the horses run at a galloping speed only over a limited distance from a goal position. Therefore, in many cases it is almost meaningless to clock an overall running time from a start point to a goal position. Namely, what are more important are the split time readings in the galloping stage of a training run. In this regard, as far as racehorse are concerned, split times are customarily measured on the basis of the furlong unit, which is about 200 meters, usually starting to take split times from an eight to six furlongs post to a goal position to acquire data for judging the racing ability or physical fitness conditions of each horse at a certain time stage of training or preparation.

Generally, stop watches are resorted to by clockers for taking split times of racehorses despite various complicate situations which take place on training tracks, including those cases where a relatively large number of horses are trained concurrently at different paces on the same track or a number of horses are jointly trained abreast of each other. In order to take split times of a particular horse or horses quickly and correctly while following their movements in such complicate situations, clocking operations usually depend on a large number of clockers which have sufficient experience and skills for coping with various situations. Therefore, there have been strong demands for a clocking system which is capable of taking and recording split times of runners like racehorses automatically and correctly in a reliable manner. As for example, in an attempt to meet such demands, there has been proposed the so-called bar-code clocking system employing a number of optical bar-code readers, which are located at the respective furlong post positions of a training track to read bar-code stickers which are bonded on saddles or other visible parts for identification of individual horses. The split times of each runner are calculated on the basis of time differentials between clock readings at the respective furlong post positions.

One of the problems with a bar-code clocker system of this sort is that it is very vulnerable to weather conditions. For instance, the bar-code reading becomes difficult or substantially infeasible in fogs and rains. Besides, racehorses are trained normally in early morning hours, starting before dawn in the winter season when the day breaks late, so that there inevitably arises a necessity for providing illumination equipments at least at a number of clocking positions, making the clocker system too large in scale as a whole. The bar-code reading also becomes difficult in case a number of horses are trained abreast of each other in such a manner as to conceal bar-code stickers behind other horses when viewed from one side of a track. In consideration of these problems or drawbacks, the bar-code clocking system has been found unsuitable for automatically clocking split times of racehorses in exercise or of other runners working together on an outdoor track. Furthermore, the bar codes serve simply to convey only a predetermined set of information, without any ability of making measurements of physical conditions of runners in work or transmitting results of measurements to bar-code readers.

In this regard, for the purpose of assessing the ability or physical fitness of runners accurately, it is important to know their physical conditions such as the number of heart beats, number of breaths or body temperature etc. especially at the time of acceleration or at the time of galloping work, in addition to and in relation with the clock readings for split times in a speeding stage of work. The data of physical conditions sampled throughout an exercise run are useful in gripping current conditions of each runner and how much work is still needed to bring the runner to fitness. However, the present inventor does not know of existence of any clocking system which is capable sampling data of physical fitness of the runners like racehorses in exercise while clocking running speeds such as split time or lap time for individual runners on a track.

SUMMARY OF THE INVENTION

Under the circumstances as explained above, it is a primary object of the present invention to provide a clocking system which is capable of automatic and accurate measurements of running speeds such as split time and lap time for a number of runners working on an outdoor track, irrespective of weather conditions.

It is another object of the present invention to provide a clocking system which can pick up data on competitiveness and physical conditions of track runners, in addition to or in relation with automatic clocking operations measuring running speeds such as split times and lap times for each runner working on a track.

It is still another object of the invention to provide a clocking system which can monitor physical conditions of individual track runners like racehorses working on a track, in relation with measurements of split times or lap times over a predetermined working distance, enabling comprehensive management of racehorses on the basis of acquired data.

It is a further object of the invention to provide a clocking system which can provide data of competitiveness and/or physical fitness conditions of a large number of racehorses in relation with clocking operations in daily exercises, permitting comprehensive management of individual horses.

In accordance with the present invention, for achieving the above-stated objectives, there is provided a clocking system fundamentally arranged to measure running speeds such as split time or lap time for a plural number of track runners at each one of a plural number of clocking positions provided at predetermined intervals along a running course or track toward a goal position, characterized in that the clocking system includes: a trigger signal transmission means provided at each one of the clocking positions and adapted to release a trigger signal toward a narrow signal receiving zone across the running track; a passing signal generating means carried by each runner and adapted to produce a passing signal at each clocking position upon reception of the trigger signal; and a measuring means provided either at each clocking position or on each runner and adapted to register a time reading upon reception of the trigger signal along with a runner identification signal and a clocking position signal.

In a preferred form of the invention, the passing signal generating means is in the form of an ID number transmitter carried by each runner and provided with an ID number generator to release a signal of an ID number specific to the runner at each clocking position upon reception of the trigger signal, and the measuring means is located at each clocking position together with the trigger signal transmission means and provided with a signal receiving section adapted to register a time reading together with a clocking position signal upon reception of the ID number signal.

In this case, preferably the measuring means includes one or a number of sensor means which are attached to the runner to collect data of physical conditions of the runner during a run on the track, and the ID number transmitter includes a data transmitting section which is connected to the sensor means and adapted to transmit the data of physical conditions along with the ID number signal from the ID number generator in a time serial fashion upon reception of a trigger signal from the trigger signal transmission means.

In another preferred form of the invention, the trigger signal transmission means is adapted to transmit a positional code signal along with the trigger signal, and the passing signal generator and measuring means are integrated into a data recorder to be carried by each runner, the data recorder including a signal receiver section for receiving the trigger and positional code signals, a clocking section for registering a time reading the instant the trigger signal is received, and a memory means for storing the positional code and the time reading along with said ID number.

In this case, similarly the measuring means is preferred to include one or a number of sensor means which are attached to the runner to collect data of physical conditions of the runner during a run along the track, and connected to the data recorder to store collected data of physical conditions in the memory means along with the positional code signal and the time reading.

For example, the above-mentioned measuring means may include electrical or ultrasonic heart beat sensor and/or breath sensor, a thermometer or a pedometer for measuring the number of heart beats and/or breath, body temperature or the number of steps in relation with the measurement of running speed and the distance run.

The above and other objects, features and advantages of the invention will become apparent from the following detailed description of the invention, taken in conjunction with the accompanying drawings which show by way of example preferred embodiments of the invention.

BRIEF DESCRIPTION OF THE DRAWINGS

In the accompanying drawings:

FIG. 5 is a diagram explanatory of different signal reception timings for reception of ID number signals;

FIG. 7 is a diagrammatic illustration of a heart beat counter which counts the number of heart beats as one barometric factor of physical conditions;

FIGS. 13(a) and 13(b) are a waveform diagram of ultrasonic signals;

FIG. 14 is a circuit diagram of a heart beat sensor;

FIGS. 17(a)–17(f) are a waveform diagram of input and output ultrasonic signals appearing in the heart beat detection process;

FIGS. 18(a)–18(d) are a diagram showing input and output waveforms of the synchronous wave detector along with input and output waves of heart beat detection circuit;

FIGS. 19(a)–19(e) are a waveform diagram of signals processed by the heat beat detection circuit;

PARTICULAR DESCRIPTION OF THE INVENTION

Hereafter, the invention is described more particularly by way of its preferred embodiments with reference to the accompanying drawings.

In each of the embodiments which are shown by the following description, the clocking system of the invention is applied to a racehorse exercising or training course for measuring split time at each one of furlong posts which are erected along the training course at intervals of 200 meters. In some embodiments, the clocking system is also used for sampling physical data of racehorses in exercise. However, it is to be understood that the present invention is not limited to the particular examples shown, and can be applied to clocking systems for automatically measuring running speeds of racing animals other than racehorses in training or to clocking systems for automatically registering lap times or split times in training or trial runs of moving objects or vehicles such as bicycles, motorbikes, motorboats, racing cars etc.

Figure 1:
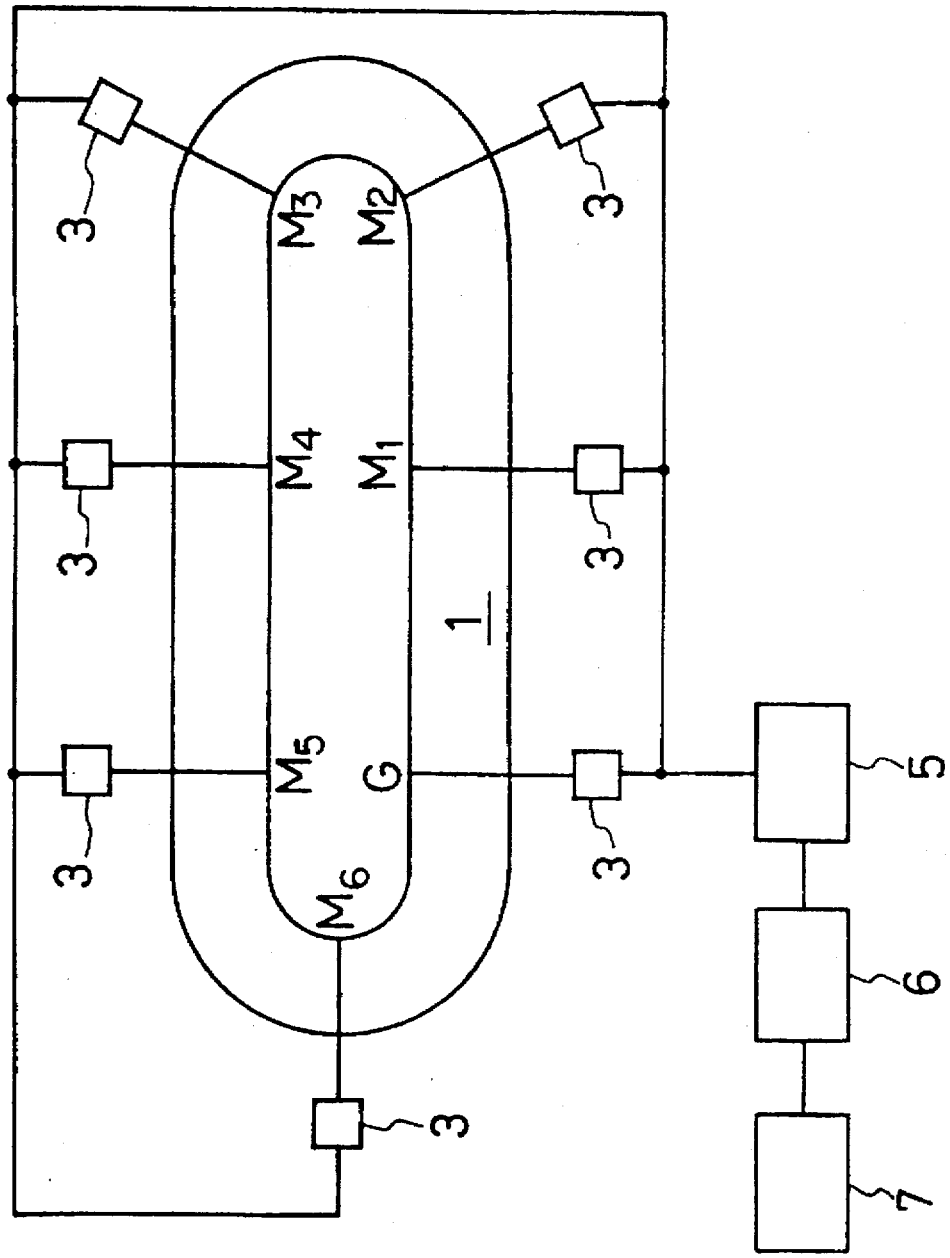
FIG. 1 diagrammatically shows general layout of a clocking system embodying the present invention.

Referring to FIG. 1, there is shown a layout of racehorse training field with a training course or track 1 for working racehorses. A number of clocking or measuring points $M_1$ to $M_n$ are provided at intervals of 200 meters along the training track 1 over a predetermined distance toward a predetermined goal position G which is a final clocking position. Instead of the training track 1 of an elliptic loop-like shape, these clocking positions $M_1$ to $M_n$ can be similarly provided along a straight training track or a sloped training track leading to a predetermined goal position.

Figure 2:
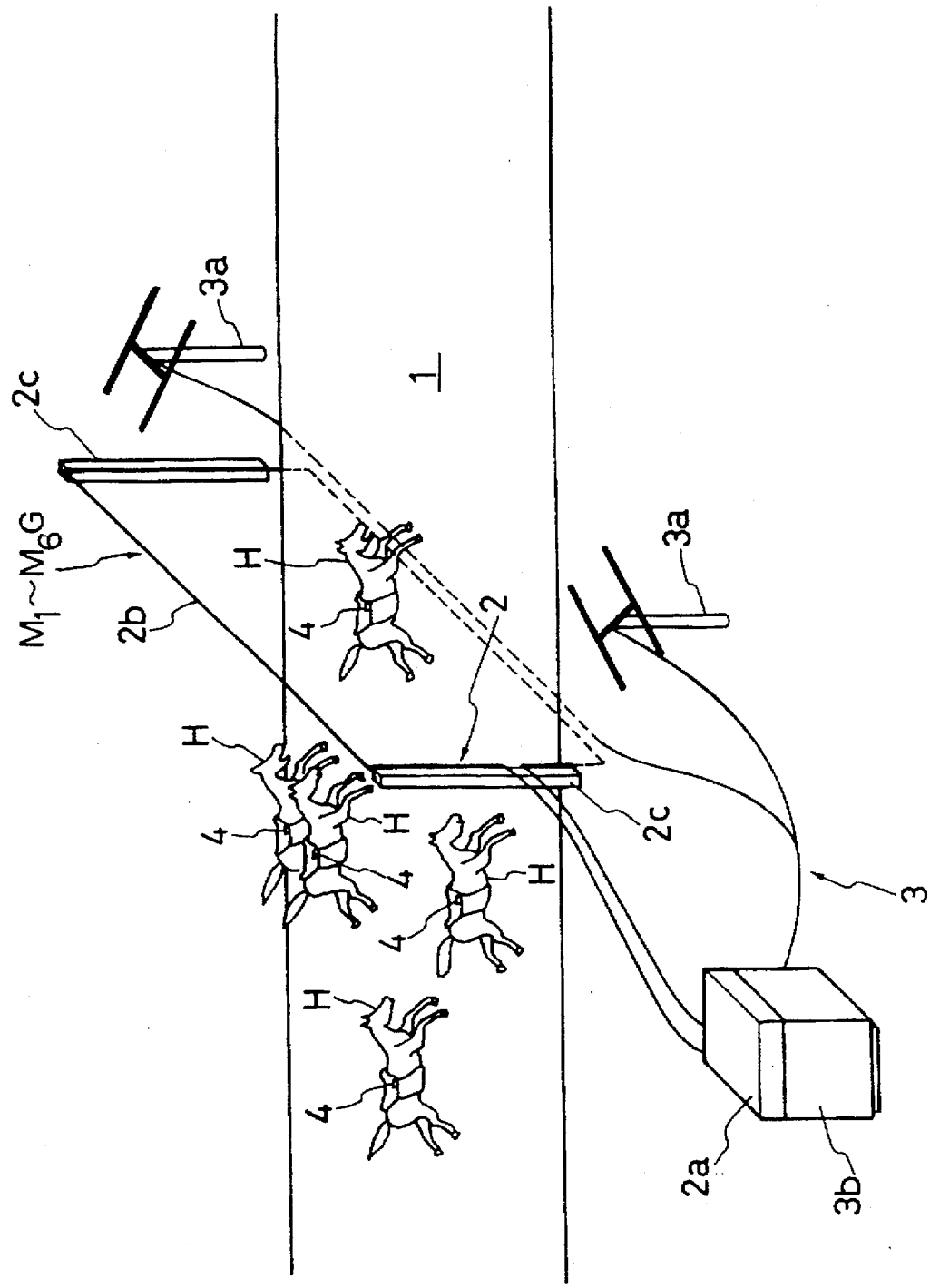
FIG. 2 is a schematic illustration explanatory of arrangements at a clocking position.

As shown in FIG. 2, in order to measure split times to the respective clocking positions $M_1$ to $M_n$ and the goal position G for individual horses H being worked on the training track 1, a trigger signal transmission means 2 and a signal reception means 3 are provided at each of the clocking positions $M_1$ to $M_n$ and at the goal position G. The trigger signal transmission means 2 is largely constituted by a signal generator 2a and a loop antenna 2b for transmission of trigger signals. In this instance, the loop antenna 2b is stretched across the training track 1, with the upper run of the loop passed around the tops of posts 2c which are erected at the opposite sides of the track 1 and with the lower run of the loop buried under the ground between the posts 2c. If desired, the loop antenna 2b may be looped in the air between the two posts 2c or looped underground across the track 1 at the measuring position. Alternatively, trigger signals may be transmitted by means of an electromagnet or ultrasonic generator. Any way, arrangements should be made to form a narrow signal receiving zone across the track at each clocking position where each one of the horses H can receive a trigger signal even if they pass by a clocking position almost simultaneously. On the other hand, the signal reception means 3 is constituted by a receiving antenna 3a and a measurement data processor 3b. The receiving antenna 3a is located at each side of the training track 1 at a position in the vicinity of the trigger signal transmission means 2. The horses H are worked on the track 1 by mounted riders (not shown). Each horse H (or its rider) carries an ID number transmitter 4 which is suitably fixed on a saddle or number cloth.

The signal generator 2a of the trigger signal transmission means 2 is arranged to produce constantly low-frequency trigger signals of about several hundreds kHz. From the loop antenna 2b which is stretched across the training track 1 at each clocking position, the trigger signals are transmitted toward the trigger signal receiving zone which has a narrow width in the running direction of the track 1. Upon crossing the narrow signal receiving zone, the ID number transmitter 4 on each horse H is actuated to transmit an ID signal by detection of a trigger signal.

Figure 3:
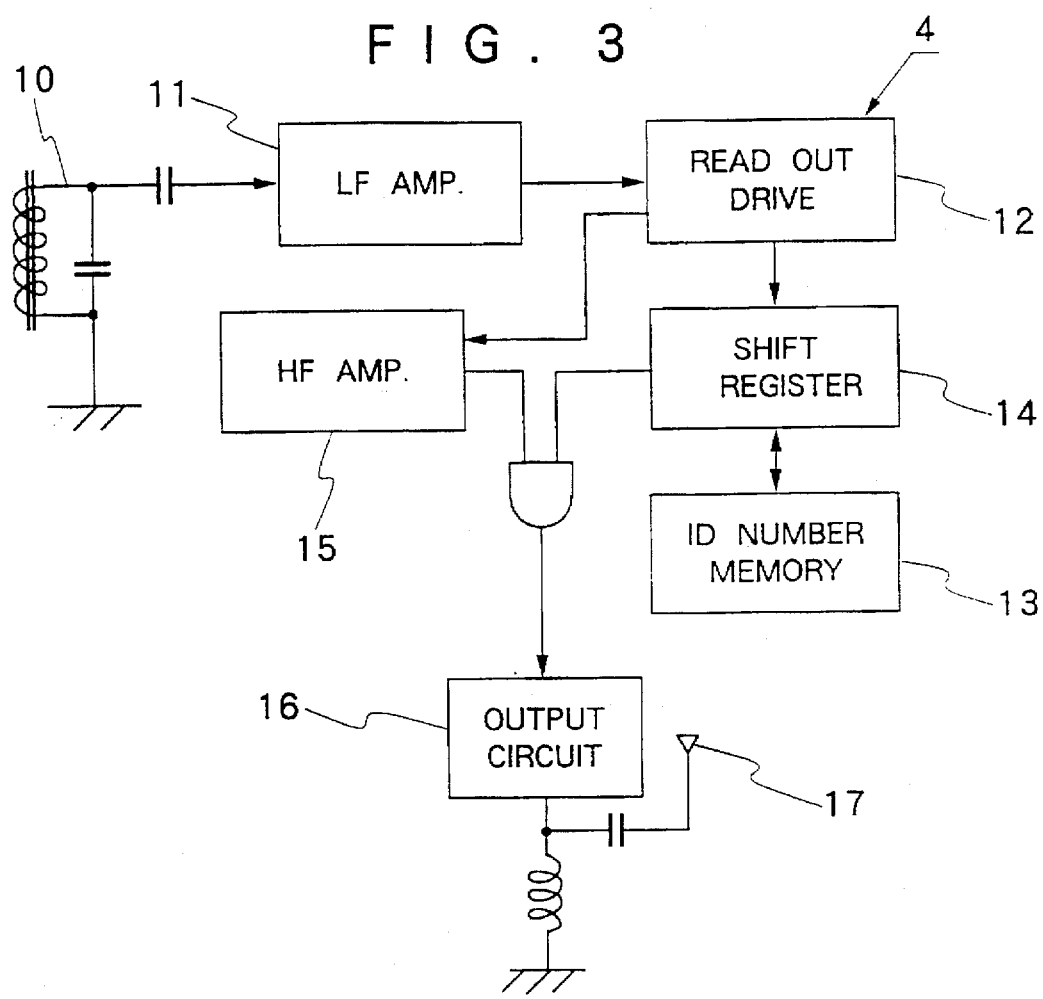
FIG. 3 is a circuit diagram of an ID number transmitter.

Shown in FIG. 3 is a circuit arrangement for the ID number transmitter 4, which includes a receiving antenna 10 and a low-frequency amplifier circuit 11. The receiving antenna 10 is tuned for reception of the trigger signal from the trigger signal transmission means 2, and a received low-frequency trigger signal is amplified by the low-frequency amplification circuit 11 to actuate a read-out drive circuit 12. Indicated at 13 is an ID number storage holding a binarized multi-bit ID number signal, which is read out by a shift register as soon as a trigger signal is fed to the read-out drive circuit 12, and put on a high-frequency signal from a high frequency generator circuit 15 to transmit an ID number signal from an output circuit 16 through an antenna 17. The ID number transmitter 4 contains a battery as a power source.

The ID number signal which is transmitted from the antenna 17 is a low level signal preferably in a frequency band from several MHz to several hundreds MHz, preferably, from several tens MHz to several hundreds MHz. In this regard, for transmission of the ID number signal, it is possible to use a signal in a several hundreds kHz or lower frequency band. Use of ID number signals of a lower frequency band is advantageous in terms of lower power consumption but it will become difficult to transmit and receive the signals at high speed, more specifically, to make time measurements in the unit of 0.01 second or in a smaller unit or to detect a large number of ID numbers concurrently at one time. On the other hand, clocking of extremely high degree of precision becomes feasible with ID number signals of a gigahertz band, which however would end up with failures in catching the ID signals by the receiving antenna due to excessively high directionability of the signals, let alone the high power consumption. In this regard, with ID number signals in a frequency band of several tens MHz to several hundreds MHz, for example, of a frequency band of about 60 MHz, it is possible to measure running speeds in the unit of 0.01 second or in a smaller unit which is sufficient in accuracy for measuring split or lap time of racehorses in work, free of reception failures attributable to high directionability of the transmitted signals. Besides, the use of a weak radio wave for the ID number signal transmission permits to suppress the energy consumption to a minimum and to fabricate the ID number transmitter 4 in a light-weight and compact form. Of course, depending upon the speed range of measurement, a radio wave in the order of kilohertz or megahertz can be employed for this purpose.

Figure 4:
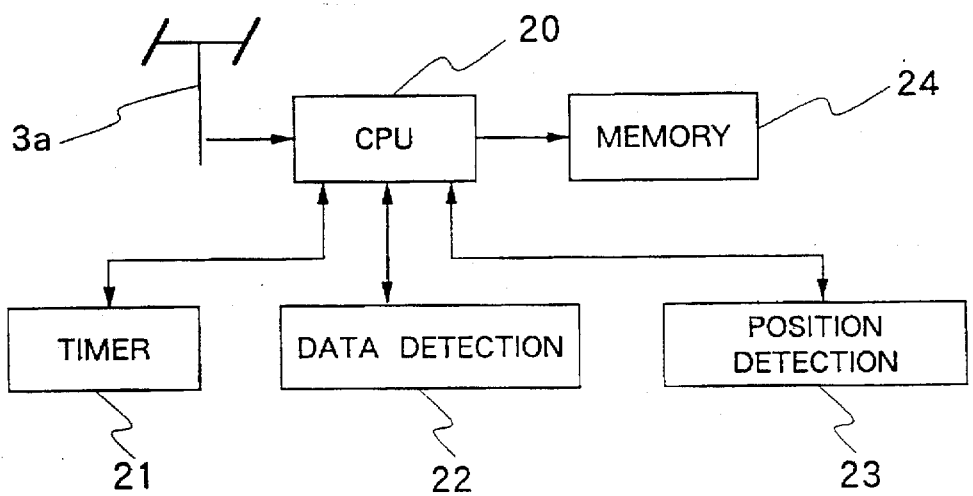
FIG. 4 is a circuit diagram of a signal reception means.

As shown particularly in FIG. 4, the measurement data processor 3b of the signal reception means 3 is constituted by a CPU 20, timer 21, data detector 22, clocking position detector 23 and memory 24. An ID number signal from the ID number transmitter 4 is received by the antenna 3a and fed to the measurement data processor 3b, whereupon the ID number is read in at the data detector 22 and stored in the memory 24 together with a reading of the timer 21 at the time of reception of the ID number signal and a clocking position signal read out from the clocking position detector 23. The contents of the memory 24, namely, the data of ID numbers, timer readings and clocking positions are sent to the controlling personal computer 5 in a suitable timing for known data processing operations to determine the readings in split time of the respective horses at each clocking position, storing compiled data in an external storage 6 which is connected to the personal computer 5. In the usual manner, the stored data of measurements can be printed out whenever necessary. Of course, from the standpoint of high-level administration of racehorses in training, it is desirable to obtain other data such as a total working time and a total distance run by each horse in addition to the clocking readings in split time or lap time, and to save such data in the personal computer 5 along with the time records of the corresponding horse at the respective clocking positions.

Regarding the clocking operation, since the signal reception means 3 is provided at a plural number of clocking positions, i.e., at the goal position G and at each of the clocking positions $M_1$ to $M_n$, it is a paramount requisite for the timers 21 on the measurement data processors 3b at the respective clocking positions to keep precisely same time. To this end, the controlling personal computer 5 is provided with a master timer 21 which controls the timers 21 on the measurement data processors 3b at the respective clocking positions to be equalized with each other in time readings during measurements of running speeds.

In the first embodiment of the invention with the above-described arrangements, an ID number transmitter 4 is put on each racehorse H in work before starting a running exercise on the training track 1. Normally, a large number of horses H are worked on the track 1 concurrently at different paces. Some horses are pushed to increase the running speed at a certain point of the track toward the goal position G. Some horses are urged into a galloping speed toward the goal position G after two or three laps of cantering around the track 1. Further, some horses finish an exercise after light canters only. In this manner, racehorses are worked depending upon the stages of training or physical conditions of individual horses. During training hours, the trigger signal transmission means 2, which are located at the respective clocking positions $M_1$ to $M_n$ and the goal position B, are constantly put in operation to transmit trigger signals sequentially toward the above-described signal receiving zones.

At the moment when a horse H runs past a clocking position, a trigger signal from the trigger signal transmission means 2 located at that clocking position is picked up by the antenna 10 of the ID number transmitter 4 which is carried by the horse H. The captured trigger signal is amplified at the low-frequency amplifier circuit 11 and fed to the read-out drive circuit 12, whereupon a read-out signal is applied to the shift register 14 to read out the ID number of the horse from the ID storage 13. Simultaneously, the signal of the read-out drive circuit 12 is also applied to the hf oscillator circuit 15 to combine and modulate a high frequency signal from the hf oscillator circuit 15 with an ID number signal as a carrier wave, for transmission from the output circuit 17 through the transmitting antenna 18 toward the receiving antenna 3a of the signal reception means 3.

Upon reception of the ID number signal of the horse H by the signal reception means 3 through its antenna 3a, this ID signal is fed to CPU 20 of the measurement data processor 3b. Simultaneously, a clock reading at the time of signal reception, i.e., a signal reception time, is fetched from the timer 21 while reading the ID number at the ID number reader 22. These data of ID number and reception time are stored in the memory 24 along with clocking position data read out from the position detector 23. These stored data in the memory 24 are read out to the controlling personal computer 5 in a suitable timing to collect and compile successively similar data for the clocking positions $M_n$ to $M_1$ with respect to each horse H in work on the track 1, recording the split time to and from each of the furlong posts $M_1$ to $M_n$ and up to the goal position G. From these data one can also know the total amount of exercise of each horse which has finished an exercise, including a total distance run and a total time of exercise.

As explained above, the ID number transmitter 4, which is carried by each horse H in work, is arranged to transmit an ID signal only when it receives a trigger signal, for suppressing its power consumption can be suppressed to a minimum. Namely, it can be used repeatedly over a long period of time even with a battery of a relatively small capacity. Besides, since the ID number transmitter 4 suffices to transmit a signal of a low level, it can be fabricated in an easily portable form, which is small in size and light in weight. Therefore, it can be easily put on a saddle or number cloth of each horse H without increasing the burden on the part of the horse to any substantial degree.

In training hours, normally a large number of horses H are worked concurrently on the track 1 at different paces. Under such circumstances, one horse may take over other horses which are being worked at a lower pace, or a plural number of horses may be worked in unison abreast of each other. Therefore, there often arises a case where a plural number of horses simultaneously pass the clocking zone at each clocking position. In such a case, there are possibilities that various ID number signals from the individual horses are indistinguishably superposed one on the other to make the ID number reading operation difficult. To cope with this problem, each ID number transmitter 4 is arranged to transmit a plural number of ID number signals on reception of a trigger signal, as shown in FIG. 5, instead of a single ID signal. Besides, desirably the respective ID number transmitters 4 are pre-adjusted to operate with different signal transmission timings from each other, for example, by setting different read-out timings for the read-out drive circuits 12 on the respective ID signal transmitters 4.

By so doing, even if a couple of ID number signals A and B are illegibly superposed one on the other at an initial point of signal reception, one ID number signal A gradually lags behind the other ID number signal B and becomes legible from its second appearance as shown in FIG. 5. In this regard, in case the ID number transmitter 4 is arranged to transmit at one time a series of five or more ID number signals on a carrier wave of several tens megahertz and in a predetermined timing, possible measurement errors can be suppressed to below 0.01 second. Accordingly, for determining the reception time of an ID number signal of one horse, the measurement data processor 3b of the signal receiver 3 may be arranged to calculate at its CPU 20 an average time of a series of ID number signals received with respect to that horse.

In addition to and in relation with the above-described operation for clocking split times or lap times of training runs, it is desirable to sample physical data of individual horses in exercise, especially, data of the so-called cardiopulmonary functions, which are extremely useful in assessing racing abilities and physical conditions of the respective horses H. In order to sample physical data of racehorses H in connection with the clocking operation, each horse H in work carries an ID number transmitter which is arranged to transmit signals of physical condition data along with an ID number signal as shown in FIG. 6.

Figure 6:
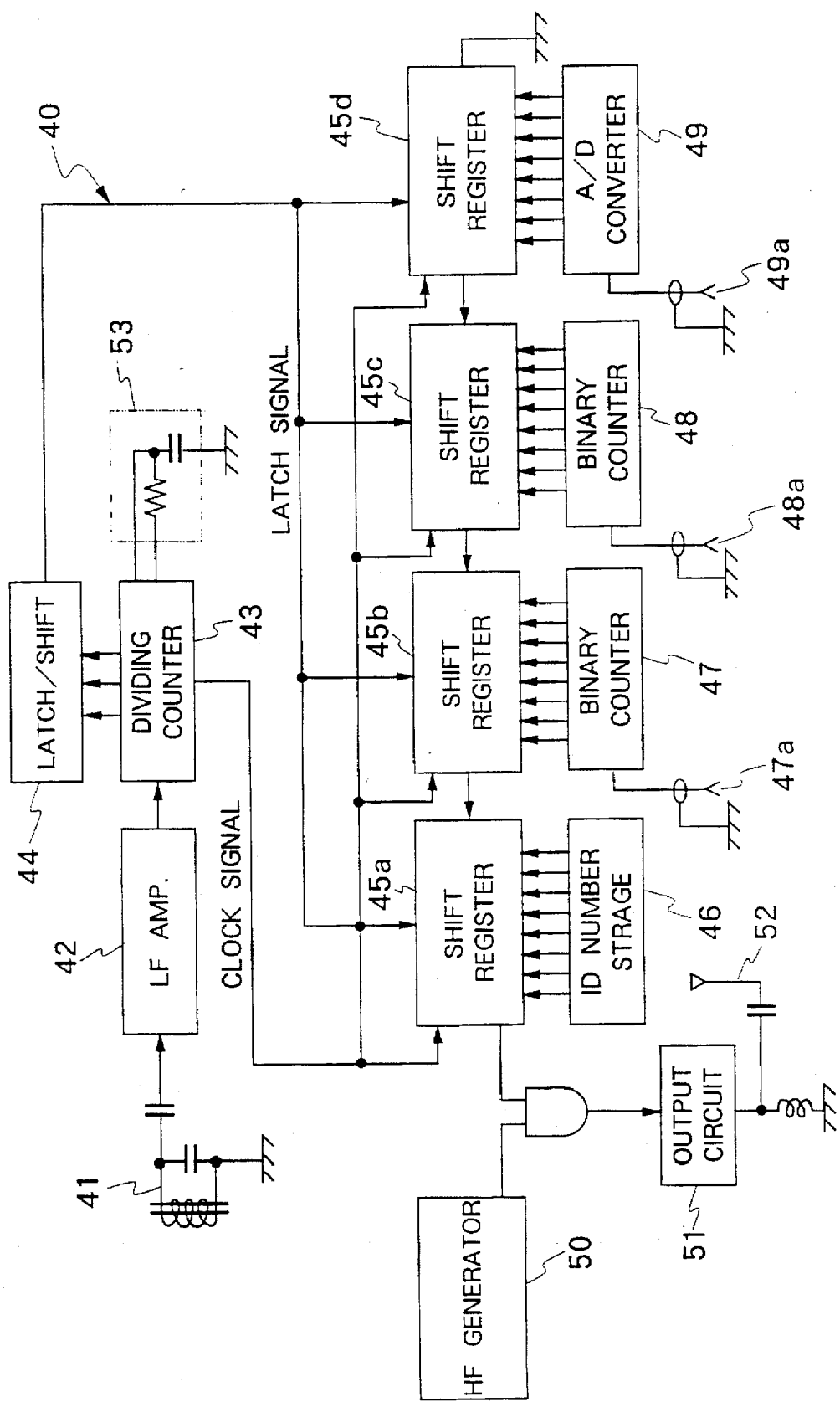
FIG. 6 is a circuit diagram of an ID number transmitter which is capable of transmitting additional data along with an ID number.

Shown in FIG. 6 is an ID number transmitter 40 which includes a receiving antenna 41 for reception of trigger signals and a low frequency amplifier circuit 42 for amplification of signals in a low frequency band which is used for the trigger signals. A trigger signal received by the lf amplifier circuit 42 is frequency-divided at a dividing counter 43 to generate a clock signal for reading out data signals. Connected to the dividing counter 43 is a latch/shift switch circuit 44 which generates latch and shift signals. On the other hand, a plural number of shift registers 45 are connected in parallel to serve as a data output section.

Four shift registers 45a to 45d, which are of the parallel-in/serial-out type, are provided in the particular embodiment shown. The first shift register 45a which serves to output ID number data is connected to an ID number storage 46. The second and third shift registers 45b and 45c are connected to input terminals 47a and 48a through binary counters 47 and 48, respectively, for the purpose of receiving a certain sort of digital data signals from outside. The fourth shift register 45d is connected to another input terminal 49a through an A/D converter 49 for receiving a certain sort of analog data signal from outside. Indicated at 50 is a high frequency generator circuit, at 51 is an output circuit, and at 52 is a transmitting antenna.

In this instance, the ID number transmitter 40, which is carried by each horse H in work, is arranged to transmit data of physical conditions of the horse H such as number of heart beats, number of breaths and body temperature along with an ID number signal. For this purpose, a heart beat sensor and a breath sensor are attached on the body of the horse H. For instance, the number of heart beats is detected by way of three electrodes $T_1$, $T_2$ and $T_3$ which are attached on the horse's skin in such a way as to circumvent its heart. Of the three electrodes $T_1$ to $T_3$, one electrode $T_1$ is connected to the ground potential and the other two electrodes $T_2$ and $T_3$ are used to detect a potential difference between two points. Differences in potential between the electrodes T2 and T3 are picked up by a differential amplifier 60, the output signal of which is shaped into a pulse signal through a signal shaper 61. The signal shaper 61 has its output terminal 62 connected, for example, to an input terminal 47a of the binary counter 47. If desired, the above-described differential amplifier and signal shaper of the heart beat sensor may be built into the ID number transmitter. In such a case, the electrodes T1 to T3 which constitute an outer sensor means are preferred to be disconnectibly connectible to the differential amplifier 60. As for a breath number sensor, although not shown in the drawings, it is possible to pick up breathing sounds by a microphone which is attached on a breast portion or neck portion of a horse under observation and to produce a pulse signal on the basis of signals from the microphone. Such a breath sensor is connected to the input terminal 48a of the binary counter 48, and its signal processing portions can be built into the ID signal transmitter 4 if desired. Further, for measurement of body temperature, for example, a thermometer in the form of a thermoelectric element like thermistor may be put on a body portion to be measured. In this regard, a thermometer which produces an analog output signal is connected to the input terminal 49a of the A/D converter 49. Other data, for instance, the number of steps taken by a horse between the respective clocking positions can be detected by the use of an acceleration sensor of the type which is employed on a pedometer. In this case, an average step length of the horse can also be obtained by dividing the number of steps by the distance between the clocking positions.

With the above-described arrangements, in order to make measurements of or to monitor physical conditions of a horse H in relation with a clocking operation for measuring running speeds, a heart beat sensor, a breath sensor and a thermometer which are operatively connected to the ID number transmitter 40 are attached on the horse body before starting an exercise on the track 1. Throughout a work on the track 1, output pulses of the heart beat sensor and breath sensor are fed to the binary counters 47 and 48, respectively, to count the numbers of heat beats and breaths in connection with the clocking operation. At the same time, signals from a thermometer which detects the body temperature of the horse H are sequentially fed to the A/D converter 48.

In this state, as the horse H passes by a clocking position, a trigger signal from the trigger signal transmission means 2 is received by the ID number transmitter 40. After amplification at the low frequency amplifier circuit 42, the trigger signal is sent to the frequency dividing counter 43 thereby to produce a clock signal. This clock signal is sent to the latch/shift switch circuit 44 which controls operations of the shift registers 45a to 45d, for reading in and out the data in the ID number storage 46 which holds an ID number, the binary counters 47 and 48 which hold the counts of the heart beat and breath numbers, respectively, and A/D converter 48 which is supplied with signals of body temperature. These data are latched in the shift registers 45a to 45d by a signal from the latch/shift switch circuit 44 upon reception of a trigger signal. Then, the latch/shift switch circuit 44 switches its operation into a shift mode, driving the shift registers 45a to 45d on the basis of clock pulses from the dividing counter 43 to read out the contents of the shift registers 45a to 45d sequentially in a time series fashion. The signals of read-out data are put on a carrier wave from the high frequency generator circuit 50 and transmitted from the output circuit 51 through the transmitting antenna 52.

In this regard, in order to repeat the above-described signal transmission, there may be provided a reset section 53 for the frequency dividing counter 43 as indicated in FIG. 6, presetting a resetting time which is longer than a time duration for the signal transmission. The frequency of repetitive signal transmissions can be varied from one ID number transmitter to another to shift signal positions of overlapped ID number signals as explained hereinbefore in connection with FIG. 5, by employing a resistor and a capacitor of different constants for the reset section 53 of a different ID number transmitter.

As explained above, when a horse H in an exercise run crosses a clocking zone in front of a clocking position where the trigger signal transmission means 2 is located, data of physical conditions such as numbers of heart beats and breaths and body temperature of the horse H are transmitted from the ID number transmitter 40 along with a signal of ID number allotted to the horse H. These signals are received by the signal reception means 3 through its receiving antenna 3a and transferred to the measurement data processor 3b and processed at CPU 20 of the measurement data processor 3b for recognition of the ID number and at the same time for determination of the data regarding the numbers of heart beats and breaths and the body temperature of the horse H, storing the ID number in the memory 25 along with the determined data of physical conditions. In this instance, the numbers of heart beats and breaths are transferred as count values to the clocking position passed, so that the numbers of heart beats and breaths between two clocking positions can be obtained by subtracting count values at a preceding clocking position from count values at a succeeding clocking position.

As clear from the foregoing description, the clocking system according to the invention makes it possible to electronically monitor their heart beat and breath numbers and body temperatures, which provide useful data for gripping their racing abilities and physical conditions when analyzed in relation with clock readings in split time or lap time. Especially, data of this sort, when accumulated over a certain training time period of a horse, will be a great help in assessing accelerative power and staying ability of that horse and also in determining the most effective menu for daily exercise. Therefore, the sampled data of physical conditions have great significance and importance when analyzed in relation with clock readings recorded in the corresponding running work.

Figure 8:
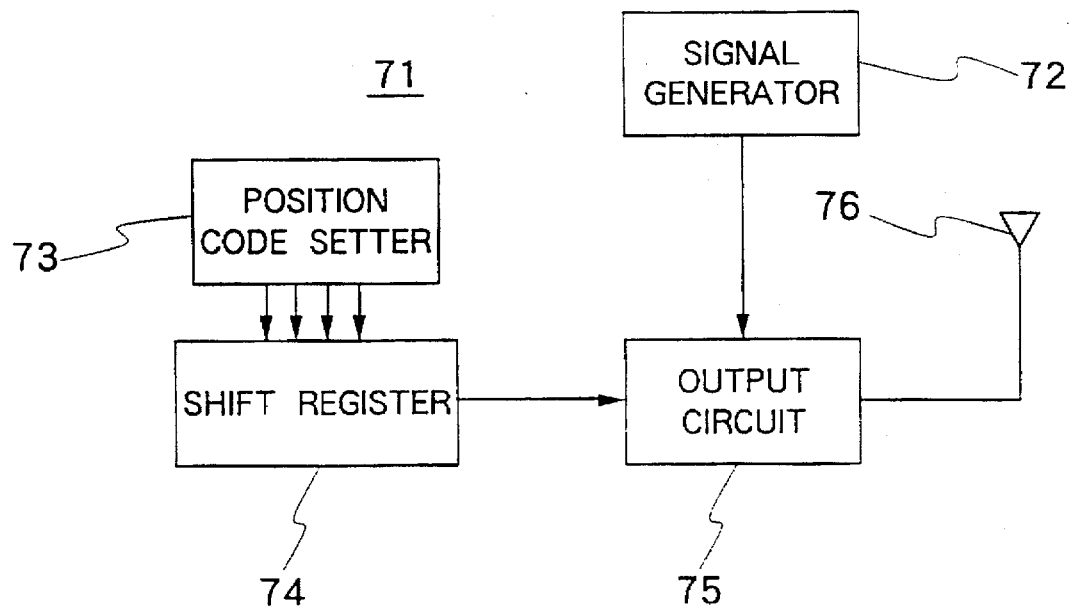
FIG. 8 is a circuit diagram of a trigger signal generating means in a second embodiment of the clocking system according to the invention.
Figure 10:
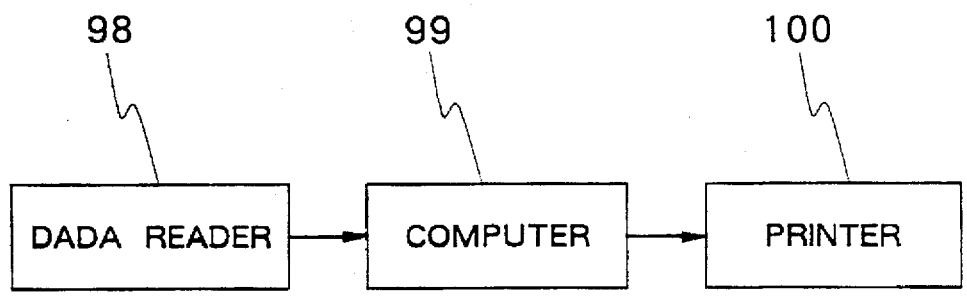
FIG. 10 is a diagram of a computerized system arrangement.
Figure 9:
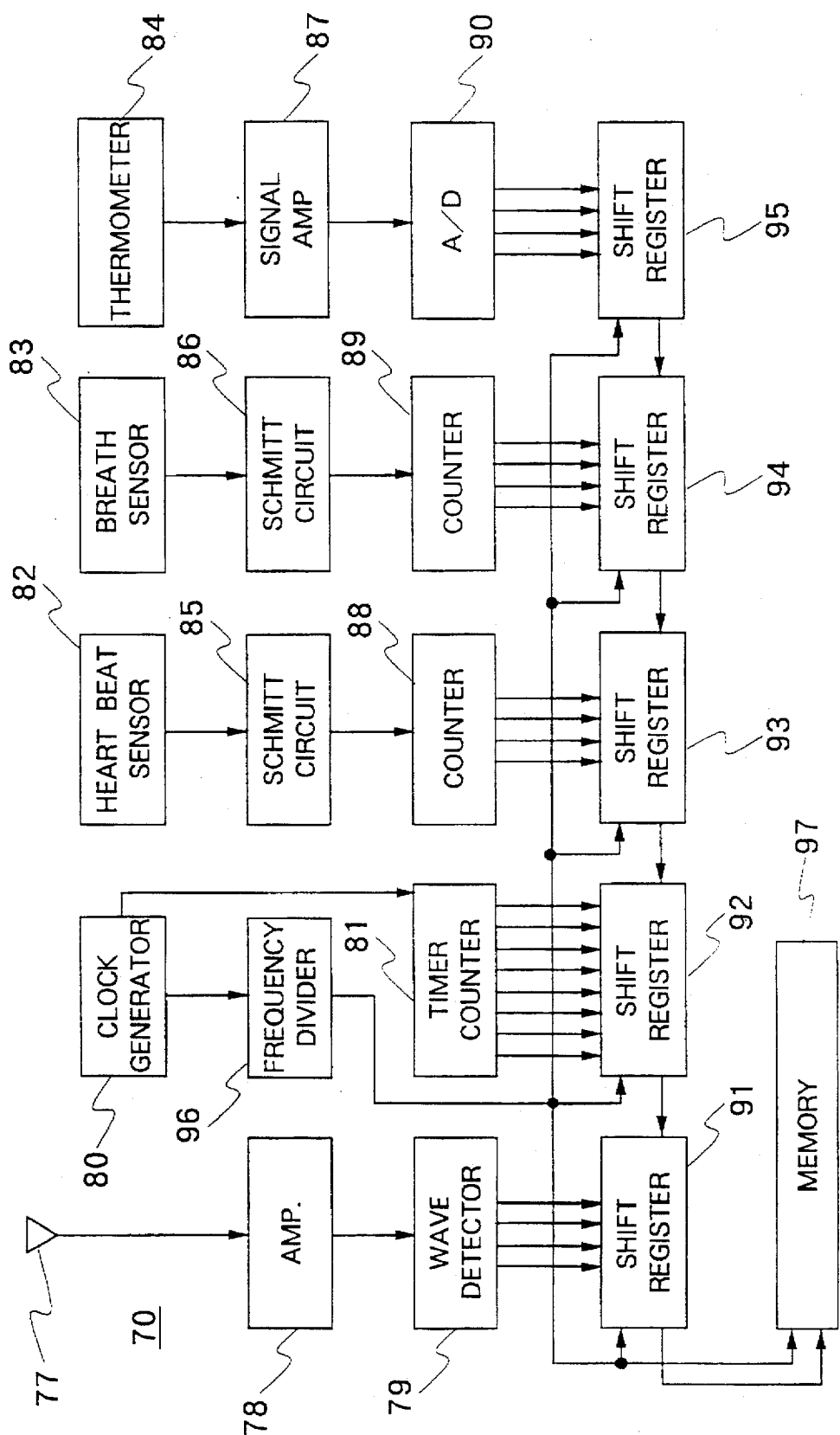
FIG. 9 is a circuit diagram of a sampled data recorder.

Referring now to FIGS. 8 to 10, there is shown a second embodiment of the invention, which includes a data recorder 70 to be carried by a runner or a horse H for detecting and recording physical condition data such as heart beat and breath numbers and body temperature along with clock readings in split time. A trigger signal transmission means is similarly located at each clocking position, but in this case it is arranged to transmit not only a trigger signal but also a code signal indicative of the clocking position where it is located.

More specifically, as shown in FIG. 8, in addition to a trigger signal generator 72, the trigger signal transmission means 71 is provided with a positional code setter 73 which produces a positional code signal. The positional code signal from the positional code setter 73 is read out through a shift register 74 and put on a carrier wave from a carrier oscillator 72 at an output circuit 75 to transmit from a loop antenna 76 a trigger signal which contains a positional code. For this signal transmission, a positional code signal is put on a weak carrier wave, for example, of a frequency of about 300 kHz repeatedly for a predetermined number of times.

On the other hand, as shown in FIG. 9, the data recorder 70 which is set on the body of a horse includes an antenna 77 which is necessary for receiving a trigger signal inclusive of a positional code in case the trigger signal transmission means 71 is arranged to transmit trigger signals wireless as described above. Therefore, in case the trigger signal transmission means employs a magnet or ultrasonic waves, it is replaced by a magnetic sensor or an ultrasonic sensor. A signal received through the antenna 77 is amplified by an amplifier 78 and fed to a wave detector 79 for recognition of a positional code signal. The data recorder 70 is further provided with a clock generator 80 which functions as a timer. Clock signals from the clock generator 80 are fed to a timer counter 81 for time measurements.

Further, for measurements of physical conditions, a heart-beat sensor 82, a breath sensor 83 and a thermometer 84 are connected to the data recorder 70 as shown in FIG. 9. Of these measuring means, the heart-beat sensor 82 and breath sensor 83 are connected to Schmitt circuits 85 and 86, respectively, while the thermometer 84 is connected to a signal amplifier 87. The Schmitt circuits 85 and 86 are connected to counters 88 and 89 thereby to count the numbers of heart beats and breaths, respectively. The signal amplifier 87 which receives an analog signal from the thermometer 84 is connected to an A/D converter to convert temperature data of the horse H into digital signals.

The data recorder 70 is arranged to read out the above-described various data upon receiving a trigger signal through its receiving antenna 77, including the data of a clocking position detected by the wave detector 79, time data detected by the timer counter 81, the data of heart beat counted by the counter 88, the data of breaths counted by the counter 89 and the body temperature data digitized through the A/D converter 90. For this purpose, similarly parallel-in/serial-out type shift registers 91 to 95 are connected to the wave detector 79, timer counter 81, counters 88 and 89 and D/A converter 90, respectively. Connected to the amplifier 78, which is connected to the receiving antenna 77, is a frequency divider 96 with a switching means which is actuated when a trigger signal is received through the antenna 77, delivering a read-out drive signal to the respective shift registers 91 to 95 from the frequency divider 96.

On delivery of the read-out drive signal, current data are read out to the respective shift registers 91 to 95, including the clocking position data from the wave detector 79 and the data of heat-beat and breath numbers and body temperature from the counters 88 and 89 and A/D converter 90. The frequency divider 96 is adapted to generate predetermined drive signals by dividing clock signals from the clock generator 80, the drive signals being applied to the respective shift registers 91 to 95 to read out the data contents sequentially therefrom. The read-out data are stored in a data storage 97 in the form of a memory device like EEPROM or RAM.

As explained above, every time a horse H passes by a clocking position, a set of data including the clocking position, clock reading, heart-beat number, breath number and body temperature are read out and stored in the data storage 97. After a running exercise, the data recorder 70 is removed and, as shown in FIG. 10, its contents are transferred to a personal computer 99 through a data reader 98, for carrying out necessary computations and compilations to present the collected data in a suitable format, for example, in the form of a table of split times to the respective clocking positions set at predetermined intervals toward a goal position, a table of heart beat and breath numbers at the respective clocking positions, a table of a total amount of work throughout a running exercise, and a table of body temperature showing variations in body temperature through the running exercise. If necessary, these tables can be printed out by the use of a printer 100.

For detection of physical conditions, ultrasonic detectors may be employed in place of the above-described heart-beat and breath sensors if desired. For example, there may be employed an ultrasonic cardiometer which is arranged to transmit ultrasonic pulses into the body of a horse during a running exercise while receiving echo signals from tissues in the path of signal transmission. An internal organ like the heart has a distinctively difference in acoustic impedance from surrounding tissues, so that distinctive reflective echoes take place at the boundaries of the heart. Besides, echo signals from the heart, which is in periodical expanding and contracting motions in contrast to other organs, are shifted in frequency by the so-called Doppler effects depending upon the speed of the expanding and contracting motions. Therefore, it is possible to detect the number of heart beats from frequency shifts of return echo signals. Similar echo signals can be obtained also from the lungs which have a different acoustic impedance from other organs and surrounding tissues. Besides, respiratory motions cause variations in air contents within alveoli of the lungs. In this regard, since ultrasonic waves undergo a greater attenuation in air than in other medium, the amplitude of return echo signals from the lung varies depending upon the alveolar air contents. Accordingly, the number of breaths can be detected by way of variations in amplitude of return echo signals from the lung.

Referring now to FIGS. 11 to 17, there is shown an ultrasonic heart beat sensor.

Figure 11:
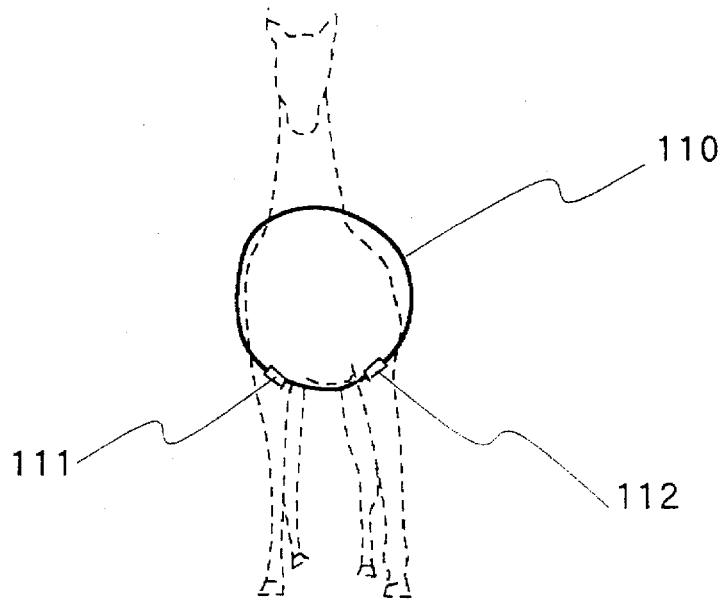
FIG. 11 is a schematic illustration of an ultrasonic sensor fitted on a horse as an alternative means for detecting the number of heart beats.
Figure 12:
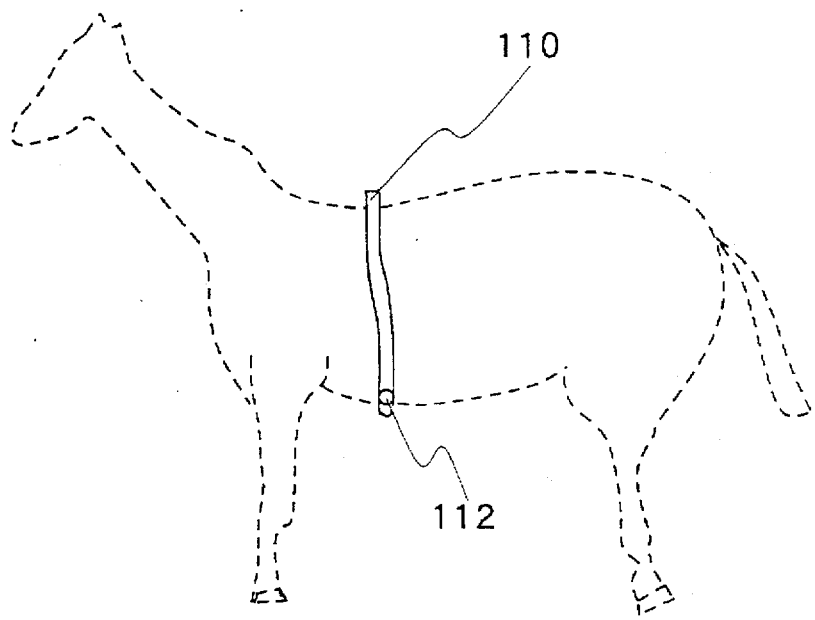
FIG. 12 is a side view of the horse in FIG. 11.

As shown in FIGS. 11 and 12, a transmitting ultrasonic transducer 111 and a receiving ultrasonic transducer 112 are attached on a girder belt of a horse H to be monitored. In this instance, the active faces of the transmitting and receiving ultrasonic transducers 111 and 112 are set in the direction of the heart of the horse H and in such a manner as to contact the outer coat of the horse H through an ultrasound transmissive medium. While ultrasonic pulses of a predetermined frequency are transmitted toward the heart from the active face of the transmitter 111, return echo signals are received by the receiver 112. For example, as shown in FIG. 13(a), an ultrasonic pulse signal consisting of four periods of 40 kHz wave is transmitted repeatedly at predetermined time intervals. In this case, rerun echo signals as shown at (b) of the same figure are received by the receiver 112. Such return echo signals contain not only echoes from boundary surfaces of the heart but also echoes from outer skin surfaces and intracorporeal tissue layers, including multiple reflection echoes. Noise components in the return echo signals can be removed by setting an echo reception time which is restricted in duration and delayed from the ultrasonic pulse signal transmission by a predetermined time lag in such a way as to focus on return echoes from the heart.

Namely, a periodical shift in frequency occurs to return echo signals from the heart which is in periodical expanding and contracting motions. Therefore, in case a sampling time is set at $t_1$, periodical wavy shifts in frequency are observed in return echoes which are received sequentially at that sampling time $t_1$, making it possible to count the number of heart beats on the basis of the frequency shifts.

Instead of using a couple of transducers 111 and 112, the operations of transmission and reception of ultrasonic signals can be performed by a single ultrasonic transducer under control of a switch means which is adapted to switch the operation of one ultrasonic transducer alternately according to predetermined transmission and reception periods.

Assuming that the sonic velocity within the body of a horse H is about 1500 m/sec and the motional speed at the surface of the heart is about 1.5 cm/sec when the horse is at rest, the frequency of return echo signals is shifted at a rate of $(1.5 \times 10^{-2}$ m/sec$)/(1500$ m/sec$) \approx 10^{-5}$ by the Doppler effects. In case ultrasonic pulse signals of 40 kHz are transmitted as mentioned hereinbefore, a frequency shift of about 40 kHz $\times 10^{-5} = 0.4$ Hz takes place. When the horse is in a running exercise, the motional speed at the surface of the heart becomes greater, as a result causing a greater frequency shift to the return echo signals. It follows that, the pace of heart beats can be-monitored by transmitting ultrasonic pulses into the body of a horse from the transmitting ultrasonic transducer 111 and detecting frequency shifts in return echo signals received by the receiving ultrasonic transducer 112. In this connection, for example, in case the transmitting and receiving ultrasound transducers 111 and 112 are located such that the length of the signal route from the transmitter 111 to the receiver 112 via the heart of a horse measures 75 cm, ultrasonic pulse signals are transmitted at time intervals of 0.5 msec. However, in consideration of possible positional deviations of the transmitter 111 and receiver 112 in actual use, it is preferable to transmit an ultrasonic pulse signal at time intervals longer than 0.5 msec.

In order to measure the number of heart beats of a horse in a running work, an ultrasonic cardiometric system as shown in FIG. 14 may be employed for this purpose. More specifically, the system of FIG. 14 includes a clock signal generator 113 which is adapted to generate a clock signal of a predetermined frequency, for example, of 40 kHz. This clock signal is fed to a transmitting transducer 111 which is driven by trigger signals from an output gate circuit 114 to transmit ultrasonic pulses at predetermined time intervals. In this regard, in a situation as described above, the drive needs to be adapted to transmit an ultrasonic pulse signal, which consists of four periods of an ultrasonic wave, at time intervals at least longer than 0.5 msec. To this end, there is provided a counter 115 which produces signals for controlling the operation of the output gate circuit 114, that is, for controlling the open periods of the output gate circuit 114 which supplies a drive signal to the transmitting transducer 111.

While ultrasonic pulse signals are being sequentially transmitted into the body of a horse, the return echo signals from intracorporeal regions, with different characteristics in acoustic impedance, are sequentially converted into electrical signals by the receiving transducer 112 and amplified at an amplifier 116. Output signals of the amplifier 116 are fed to an input gate circuit 117 which is opened in a predetermined gating timing on the basis of signals from the counter 115 to take in return echo signals only in a predetermined sampling time. In this instance, a sampling time $t_1$ is set to recur in a suitable timing after transmission of an ultrasonic pulse signal to focus the sampling range to a point of observation, taking into consideration the body size and the heart position in the body of a horse H as well as possible deviations of the transmitting and receiving transducers 111 and 112 from predetermined setting positions. Noise contents in the return echo signals can be removed almost completely by using a very short sampling time, which however gives rise to a necessity for shifting the sampling timing forward or backward in each case depending upon the body size of a horse to be monitored, that is, depending upon the distance from the transmitting and receiving transducers 111 and 112 to the heart to be monitored. In contrast, a longer sampling time can always hold a target point within its sampling range without any adjustment, despite differences in body size between individual horses or differences in distance from the heart to the transmitting and receiving transducers 111 and 112. Therefore, the length of sampling time should be determined in consideration of possible variations in the distance to and from the heart. However, at the same time one should be aware of the fact that a longer sampling time means a greater noise content. In this regard, in contrast to the heart which is in periodical expanding and contracting motions, substantially no frequency shifts are detectible in return echoes from tissues of internal organs and muscles around the heart, so that detection errors can be prevented by extracting only frequency shifts in return echoes in signal processing operations as will be described hereinlater.

Figure 15:
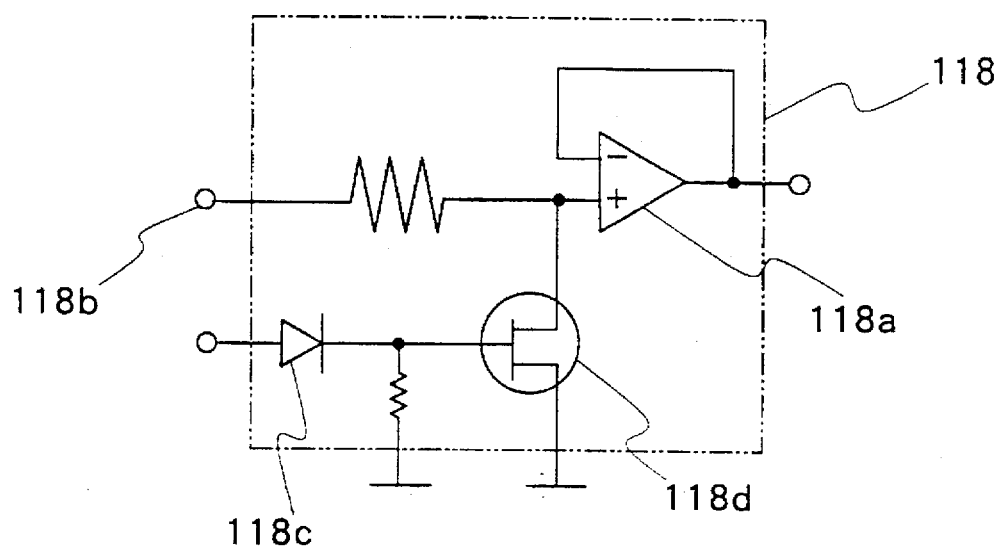
FIG. 15 is a circuit diagram of a synchronous wave detector.

Signals which have been passed through the input gate circuit 117 are fed to a synchronous wave detector 118 thereby to detect phase deviations of frequencies of received echo signals from the frequency of transmitted ultrasonic pulse signals. For this purpose, the synchronous detector 118 can be arranged as shown in FIG. 15. More specifically, in the particular example shown, the synchronous detector 118 includes an operational amplifier 118a which is provided with an input terminal 118a and, in parallel therewith, a Schottky barrier diode 118c and an FET 118d on a signal line which is supplied with a clock signal from the clock signal generator 113. When the clock signal is "high", FET 118d is turned ON to ground the positive terminal of the operational amplifier 118a. Accordingly, there would occur a variation in average potential should the return echo signals to the input terminal 118b contain deviations in phase relative to the reference clock signal, and the operational amplifier 118a would produce an output signal which likewise contains deviations in phase. The phase-shifted signal is passed through a low-pass filter 119 to obtain a signal of a predetermined waveform containing a phase shift attributable to the motion of the heart. This phase-shifted signal is fed to a heart beat detection circuit 120 for detection of the number of heart beats.

Figure 16:
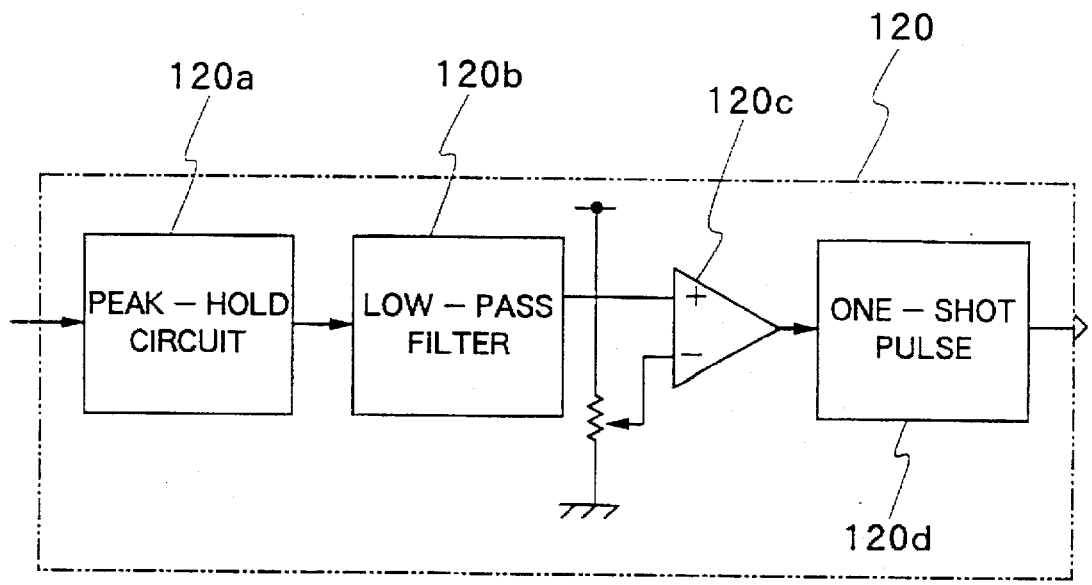
FIG. 16 is a block diagram of a heart beat detection circuitry.

In this instance, as shown in FIG. 16, the heart beat detection circuit 120 includes a peak hold circuit 120a, a low-pass filter 120b and a comparator 120c. A signal from the afore-mentioned low-pass filter 119 is passed through the peak hold circuit 120a to hold its peak value, and, after waveform shaping through the low-pass filter 120b, it is compared with a threshold value at the comparator 120c. In case the signal is higher than a predetermined level, a one-shot pulse circuit 120d is actuated to output a pulse indicative of a heart beat. Thus, data of heart beats of a horse H in a running exercise can be collected in relation with a clocking operation by connecting the heart beat detection circuit 120 to the input terminal 47a of the binary counter 47 on the ID number transmitter 40 of the above-described first embodiment or to the Schmitt circuit 85 of the data recorder 70 of the second embodiment.

The detection of the number of heart beats is explained in greater detail below with reference to timing charts of FIGS. 17 and 18.

Firstly, shown at (a) of FIG. 17 is a clock signal of a predetermined frequency which is produced by the clock signal generator 113, and at (b) of FIG. 17 is a gating signal which is supplied from the counter 115 to the output gate circuit 114 at predetermined time intervals on the basis of the clock signal to open the gate each time for a predetermined time period. Indicated at (c) of FIG. 17 is an ultrasonic pulse signal which is periodically transmitted into the body of a horse from the transmitting transducer 111.

On the part of the receiving transducer 112, return echoes of the transmitted pulse signals are converted into electrical signals as shown at (d) of FIG. 17. These return echo signals consist of reflection echoes from various intracorporeal portions with different acoustic impedance characteristics, which exist along the path of the ultrasonic signal transmission. Of the return echo signals, echoes from the heart exist in a range which corresponds to the distances from the heart to the transmitting and receiving transducers 111 and 112. Namely, after transmission of an ultrasonic pulse signal from the transmitting transducer 111, return echo signals from the heart are received by the receiving ultrasonic transducer 112 with a time lag which corresponds to the distances from the heart to the transmitting and receiving transducers 111 and 112. In order to extract the heart echoes alone, a signal as shown at (e) of FIG. 17 is fed from the counter 115 to the input gate trigger circuit 117 thereby to open its gate at a predetermined sampling time $t_1$. As a result, as shown at (f) of FIG. 17, ultrasonic echo signals are output to the synchronous wave detector 118 from the input gate circuit 117 each time for a predetermined time period.

At the synchronous detector 118, the received echo signals are checked for a frequency shift from a reference clock signal from the clock signal generator 113. Shown on an enlarged scale at (a) of FIG. 18 is an input signal which is supplied to the synchronous detector 118 during the sampling period indicated at (f) FIG. 17. This input signal is compared with the clock signal (shown at (b) of FIG. 18) supplied from the clock signal generator 113, to check for a phase shift from the latter. In case the input signal is shifted in phase, a signal of a waveform as shown at (c) of FIG. 18 is produced in the output stage of the synchronous detector 113. This output signal is rectified and passed through the low-pass filter 119 to get a signal of a waveform as indicated by a solid line at (d) of FIG. 18.

The heart becomes almost motionless at the moment when it reaches the most contracted or expanded state, and therefore no phase shift occurs to sampled return echo signals until the heart begins to expand from the most contracted state or to contract from the most expanded state. A maximum phase shift appears when the heart goes into most dynamic motions. In this regard, in case the output signal of the low-pass filter 119 is of a waveform as indicated at (a) of FIG. 19, the peak-hold circuit 120a produces an output signal which holds the peaks as shown at (b) of FIG. 19. The letter "R" indicates a reset period. That output signal of the peak-hold circuit 120a is passed through the low-pass filter 120b to shape the signal waveform as shown at (c) of FIG. 19, which is then compared with a threshold value at the comparator 120c to obtain an output signal of a waveform as shown at (d) of FIG. 19. Upon detecting a rise in the signal of FIG. 19(d), the one-shot pulse generator 120d produces a one-shot pulse as indicated at (e) of FIG. 19, which is supplied to the binary counter 47 or the Schmitt circuit 85 to add to the number of heart beats.

Figure 20:
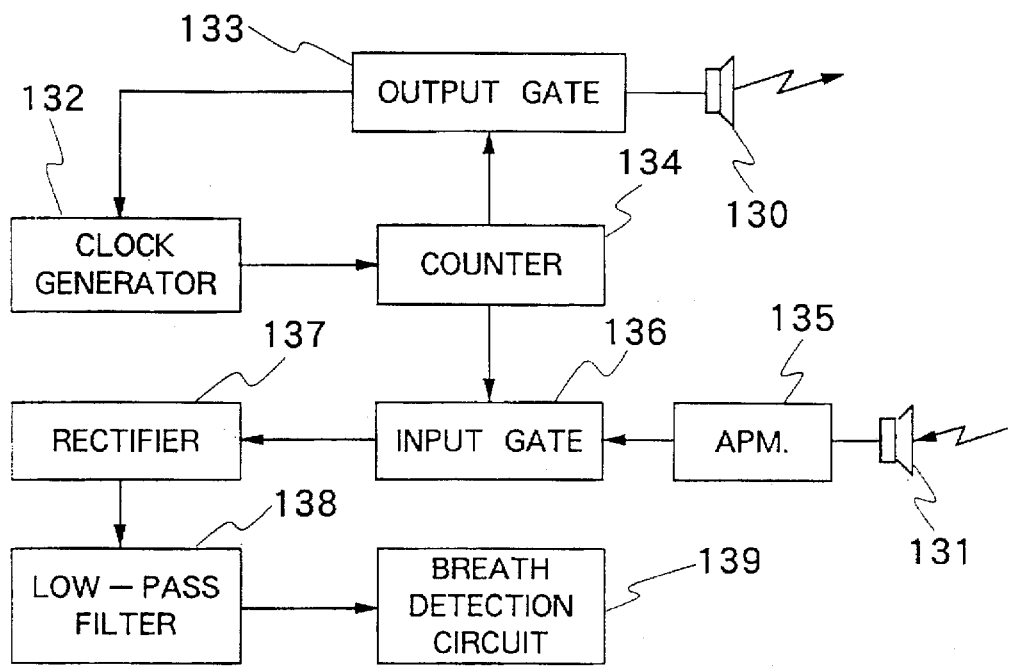
FIG. 20 is a circuit diagram of a breath sensor for sampling the number of breaths as another barometric factor of physical conditions.

For detection of breath numbers, there may be employed a breath sensor with a circuit arrangement as shown in FIG. 20. In this instance, major parts of the circuit arrangement are basically same as in the heart beat sensor of FIG. 14.

In FIG. 20, indicated at 130 is a transmitting ultrasonic transducer, and at 131 is a receiving ultrasonic transducer. The transmitting and receiving transducers 130 and 131 are set in position with their active faces turned toward the lung of a runner to be monitored. The breath sensor includes, on its ultrasonic pulse transmission side, a clock signal generator 132, an output gate circuit 133 and a counter 134. These components perform the same functions as their counterparts in the heart beat sensor circuitry shown in FIG. 14. Similarly, the breath sensor includes, on its return echo reception side, an amplifier 135 and an input gate circuit 136 which likewise serve for the same purposes as the counterparts in the heart beat sensor circuitry of FIG. 14. In this case, however, a sampling time, when the gate of the input gate circuit 136 is opened for passing on return echo signals from the lung, is set at time t2 of FIG. 13(b).

The number of breaths is detected on the basis of variations in alveolar air contents. Since ultrasonic echo signals undergo attenuations to a certain degree depending upon the amount of intervening air, return echoes from the lung exhibit variations in amplitude in relation with the respiratory motions of the lung. Therefore, output signals from the input gate circuit 136 are passed through a rectifier 137 and a low-pass filter 138 to detect the number of breaths at a breath detection circuit 139 on the basis of variations in amplitude. The breath detection circuit 139 is connected either to the input terminal 48a of the binary counter 48 in the first embodiment described above or to the Schmitt circuit 86 of the data recorder 70 in the second embodiment to count the number of breaths in relation with the clocking operation.

Figure 21A:
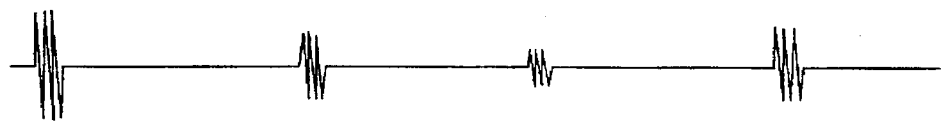
FIGS. 21(a)–21(c) are a waveform diagram of signals appearing in the breath detection process.
Figure 21B:
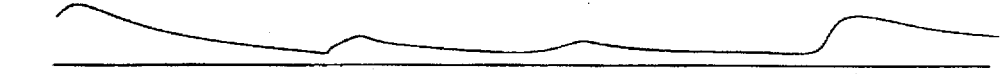
Figure 21C:
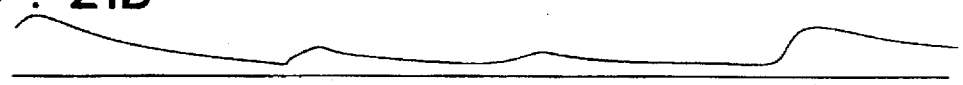

In an exhalation phase, return echo signals from the lung, which are supplied to the rectifier 137 through the input gate circuit 136, pick up amplitude because of reductions in the alveolar air contents which tend to attenuate ultrasonic signals. On the other hand, in an inhalation phase, return echo signals are attenuated in a greater degree by increasing alveolar air contents. Therefore, input echo signals coming in through the input gate circuit 136 contain periodical changes in amplitude as shown at (a) of FIG. 21. Through the rectifier 137, these input signals are shaped into a waveform as shown at (b) of FIG. 21. The output signal of the rectifier 137 is then passed through the low-pass filter 138 to obtain a signal of a waveform as shown at (c) of the same figure. This signal (FIG. 21(c)) is fed to the breath sensor circuit 139 and compared with a predetermined threshold value to produce a one-shot pulse upon detection of a signal level corresponding to one respiratory motion. Each one-shot pulse is fed to the binary counter 48 or Schmitt circuit 86 to add to the number of breaths.

The above-described ultrasonic heart beat sensor can detect the number of breaths of a horse accurately despite the body motions during a running exercise particularly when an ultrasound transmissive jelly or a similar material is applied between the outer coat of the horse and the ultrasonic transducer or transducers, without necessitating the horse's coat hair, in contrast to an electrical cardiometer or heart beat sensor which normally requires to shave the coat hair to avoid contact failures of electrode pads. Further, the application of ultrasonic waves to the detection of breath number contributes to enhance the detection accuracy to a marked degree because it is free from noises as will be picked up when using a microphone as a sensor.

Furthermore, the above-described clocking system with a heart beat sensor and/or a breath sensor is useful for measuring the time length over which the heart beating and/or breathing of each horse settles down to a normal pace after a running exercise.

What is claimed is:

1. A clocking system for measuring running speeds of a plural number of track runners at each one of a plural number of clocking positions provided at predetermined intervals along a running course or track toward a goal position, said clocking system comprising:

an ID number transmitter carried by each runner and provided with an ID number generator to release at least an ID signal of said runner at each clocking position;

a trigger signal generator means provided at each one of said clocking positions to release a trigger signal toward said ID number transmitter of said runner passing across a measuring zone in front of said clocking position; and time measuring means located at each one of said clocking positions to receive said ID signal transmitted by said ID number transmitter in response to said trigger signal from said trigger signal generator means, and arranged to register Identity of said runner passing across said clocking position along with a split time to said clocking position;

said ID number transmitter being arranged to release said ID signal repeatedly for a plural number of times in response to a trigger signal at predetermined time Intervals distinguishable of ID signals from other ID number transmitters carried by other runners.

2. A clocking system as defined in claim 1, wherein said ID number transmitter is arranged to repeat said ID signal for at least five times in response to a trigger signal, and said measuring means Is arranged to compute a mean value of reception times of repeated ID signals as a time reading in split time of said runner.

3. A clocking system as defined in claim 2, wherein said ID number transmitter is arranged to transmit said ID signal on a frequency higher than several tens MHZ and at time intervals smaller than 0.1 second.

4. A clocking system as defined in claim 1, wherein said trigger signal generator means is constituted by a member selected from the group consisting of a low frequency transmission antenna, an ultrasonic transducer and an electromagnet.

5. A clocking system as defined in claim 1, wherein said ID number transmitter comprises, in addition to an ID number transmitting section, a data transmitting section for transmission of data of physical conditions of said runner, said data transmitting section being connected to a physical sensor means attached to said runner, and arranged to transmit physical data in time series along with said ID signal upon receipt of a trigger signal from said trigger signal generator means.

6. A clocking system as defined in claim 5, wherein said physical sensor means is arranged to take physical data at least in heart beat, respiration, step distance and body temperature in case said runner is a biotic athlete thereby to evaluate physical fitness of said runner on the basis of said time reading and physical data.

7. A clocking system as defined in claim 6, wherein said physical sensor means is an electrical cardiometric sensor having three electrodes attached around the heart of said runner for detecting a number of heart beats of said runner over a predetermined distance, two of said electrodes being connected to a differential amplifier while the remaining one of said electrodes is retained at the earth potential.

8. A clocking system as defined in claim 6, wherein said physical sensor means is an ultrasound cardiometric sensor having an ultrasound transducer for transmitting ultrasound pulses toward the heart of said runner, and an ultrasound signal processor for detecting a number of heart beats of said runner over a predetermined distance on the basis of frequency shifts of ultrasound echoes from said heart.

9. A clocking system as defined in claim 6, wherein said physical sensor means Is provided with a microphone attached in the vicinity of a respiratory passage of said runner.

10. A clocking system as defined in claim 6, wherein said physical sensor means is an ultrasound breath sensor having an ultrasound transducer for transmitting ultrasound pulses toward the lung of said runner, and an ultrasound signal processor for detecting a number of breaths of said runner over a predetermined distance on the basis of variations In amplitude of ultrasound return echoes from said lung.

11. A clocking system as defined in claim 6, wherein said physical sensor means is provided with a pedometer employing an acceleration sensor for detecting a number of steps taken by said runner over a predetermined distance.

12. A clocking system as defined in claim 6, wherein said physical sensor means is a thermometer.

* * * * *